United States Patent
Zhang et al.

(10) Patent No.: US 12,403,107 B2
(45) Date of Patent: Sep. 2, 2025

(54) LIPID PHARMACEUTICAL PREPARATION AND APPLICATION THEREOF

(71) Applicant: HUZHOU INNOVATION PHARMACEUTICAL CO., LTD., Zhejiang (CN)

(72) Inventors: Jie Zhang, Zhejiang (CN); Peike Tang, Zhejiang (CN)

(73) Assignee: HUZHOU INNOVATION PHARMACEUTICAL CO., LTD., Zhejiang (CN)

( * ) Notice: Subject to any disclaimer, the term of this patent is extended or adjusted under 35 U.S.C. 154(b) by 939 days.

(21) Appl. No.: 17/603,015

(22) PCT Filed: Apr. 15, 2020

(86) PCT No.: PCT/CN2020/084832
§ 371 (c)(1),
(2) Date: Oct. 12, 2021

(87) PCT Pub. No.: WO2020/211762
PCT Pub. Date: Oct. 22, 2020

(65) Prior Publication Data
US 2022/0193014 A1    Jun. 23, 2022

(30) Foreign Application Priority Data
Apr. 15, 2019   (CN) .......................... 201910299949.9

(51) Int. Cl.
| A61K 31/167 | (2006.01) |
| A61K 9/00 | (2006.01) |
| A61K 9/06 | (2006.01) |
| A61K 31/155 | (2006.01) |
| A61K 31/245 | (2006.01) |
| A61K 31/381 | (2006.01) |
| A61K 31/445 | (2006.01) |
| A61K 31/47 | (2006.01) |
| A61K 45/00 | (2006.01) |
| A61K 45/06 | (2006.01) |
| A61K 47/24 | (2006.01) |
| A61K 47/28 | (2006.01) |
| A61K 47/36 | (2006.01) |
| A61K 47/44 | (2017.01) |
| A61P 23/02 | (2006.01) |
| A61P 29/00 | (2006.01) |
| A61P 31/02 | (2006.01) |
| A61P 31/04 | (2006.01) |

(52) U.S. Cl.
CPC .......... *A61K 31/167* (2013.01); *A61K 9/0014* (2013.01); *A61K 9/06* (2013.01); *A61K 31/155* (2013.01); *A61K 31/245* (2013.01); *A61K 31/381* (2013.01); *A61K 31/445* (2013.01); *A61K 31/47* (2013.01); *A61K 45/00* (2013.01); *A61K 45/06* (2013.01); *A61K 47/24* (2013.01); *A61K 47/28* (2013.01); *A61K 47/36* (2013.01); *A61K 47/44* (2013.01); *A61P 23/02* (2018.01); *A61P 29/00* (2018.01); *A61P 31/02* (2018.01); *A61P 31/04* (2018.01)

(58) Field of Classification Search
None
See application file for complete search history.

(56) References Cited

U.S. PATENT DOCUMENTS

| 4,647,586 A | 3/1987 | Mizushima et al. |
| 5,227,165 A | 7/1993 | Domb et al. |
| 5,912,271 A | 6/1999 | Brodin et al. |
| 2005/0287180 A1 | 12/2005 | Chen |
| 2008/0139392 A1 | 6/2008 | Acosta Zara et al. |
| 2018/0228903 A1* | 8/2018 | Kohane ................. A61K 47/20 |
| 2018/0265523 A1* | 9/2018 | Sengupta ............. C07D 311/22 |
| 2020/0197227 A1* | 6/2020 | Locke ................... A61L 26/008 |
| 2022/0110923 A1* | 4/2022 | Thomson ............... A61K 31/44 |

FOREIGN PATENT DOCUMENTS

| CN | 1152873 A | 6/1997 |
| CN | 101027065 A | 8/2007 |
| CN | 101636148 A | 1/2010 |
| CN | 102933200 A | 2/2013 |
| CN | 103705439 A | 4/2014 |
| CN | 108354903 A | 8/2018 |
| CN | 108379269 A | 8/2018 |
| CN | 108743952 A | 11/2018 |
| CN | 102892408 A | 1/2023 |
| WO | 03077885 A2 | 9/2003 |

OTHER PUBLICATIONS

English translation for CN 108743952 A (Year: 2018).*
Nov. 21, 2022 Chinese First Office Action issued in Chinese Patent Application No. 2019102999499.
Nov. 16, 2022 Chinese First Office Action issued in Chinese Patent Application No. 2020800219737.
Jun. 10, 2023 Chinese Second Office Action issued in Chinese Patent Application No. 202080021973.7.

(Continued)

*Primary Examiner* — Sin J Lee
(74) *Attorney, Agent, or Firm* — Houston Beshining Law Office PLLC; Liangang Ye

(57) ABSTRACT

A lipid pharmaceutical preparation and application thereof. The lipid pharmaceutical preparation comprises a local anesthetic and a lipid substance. The mass percentage of the local anesthetic in the lipid pharmaceutical preparation is 2%-50%. The local anesthetic is lidocaine, tetracaine, bupivacaine, articaine, cinchocaine, dibucaine, etidocaine, levobupivacaine, mepivacaine, prilocaine, ropivacaine, trimecaine, benzocaine, or procaine. The mass percentage of the lipid substances in the lipid pharmaceutical preparation is 30%-98%. The sum of the mass percentages of the components in the lipid pharmaceutical preparation is 100%. In general analgesic application, the lipid pharmaceutical preparation can produce continuous and safe analgesic effects for 12, 24, 36, 48, or 72 hours, or even longer.

19 Claims, No Drawings

(56) References Cited

OTHER PUBLICATIONS

Jul. 15, 2020 International Search Report issued in International Patent Application No. PCT/CN2020/084832.
Jul. 15, 2020 Written Opinion of the International Searching Authority issued in International Patent Application No. PCT/CN2020/084832.
Jul. 11, 2025 Chinese Second Office Action issued in Chinese Patent Application No. 2019102999499.

* cited by examiner

LIPID PHARMACEUTICAL PREPARATION AND APPLICATION THEREOF

The present application is a National Stage of International Application No. PCT/CN2020/084832, filed on Apr. 15, 2020, which claims the priority of Chinese Patent Application CN201910299949.9 filed on Apr. 15, 2019, the contents of which are incorporated herein by reference in their entireties.

TECHNICAL FIELD

The present disclosure relates to a lipid pharmaceutical preparation and an application thereof.

BACKGROUND

Local anesthetic preparations are used to prevent or treat the pain on skin or mucosa, for example: 2% of lidocaine hydrochloride gel is used to relieve pain associated with sunburn; EMLA cream, an emulsion containing eutectic mixture of lidocaine and prilocaine, is used for anesthesia of intact skin before surgery that can cause pain; Lidoderm is a solidified gel patch containing 5% of lidocaine, which is used to relieve postherpetic neuralgia (the skin itself is intact); Pliaglis cream, an emulsion containing eutectic mixture of 7% of lidocaine and 7% of tetracaine, is used for anesthesia of intact skin before surgery that can cause pain. However, the above-mentioned local anesthetic preparations have their own serious limitations. For example: lidocaine hydrochloride gel cannot anesthetize intact skin; prilocaine in EMLA may cause methemoglobinemia; tetracaine in Pliaglis may cause anaphylaxis related to ester local anesthetics, and tetracaine can be hydrolyzed, so Pliaglis must be stored in refrigeration to reduce the rate of hydrolysis; Lidoderm cannot anesthetize intact skin within 120 minutes or even 4 hours, and Lidoderm cannot be used for more than 12 hours each time. In addition, the common limitation of the above-mentioned local anesthetic preparations is that they cannot achieve long-term continuous and safe analgesic effect.

In the treatment of many diseases, the ideal product is able to have continuous analgesic effect for 6, 12, 18, 24, 30, or even 48 hours or longer. Therefore, a pharmaceutical preparation with safe and long-term continuous analgesic effect is needed urgently.

The surfaces of human tissue that are not covered by skin or mucosa, such as surgical incision, burn and scald surface, trauma surfaces, etc., (open human body surfaces) often have analgesic needs. The characteristic of the open human body surfaces is the absorption of external substances, such as the absorption of local anesthetics, without the barriers like skin. (In the present disclosure, "open human body surface" or "open human tissue surface" refers to the surface of human tissue not covered by skin or mucosa, or the surface of human tissue covered by incomplete skin or mucosa (such as damaged skin or mucosa), including stitched and unstitched surgical incision wounds). Therefore, if a local anesthetic preparation without sustained-release function is placed on an open human body surface, for example, after 2% of lidocaine hydrochloride solution commonly used in hospitals is applied on the burn surface, the local anesthetic contained in the preparation will be quickly absorbed into the systemic blood circulation, resulting in high blood concentrations that may cause serious side effects, and a short duration of analgesic effect. For this reason, a pharmaceutical preparation that can achieve a sustained-release effect is needed urgently.

Postoperative incision analgesia is a common requirement. Nowadays, the commonly used method is to use analgesic pumps to deliver drugs that act on the central nervous system, such as fentanyl and demerol, into the patient's body. These drugs pass through the blood-brain barrier and then enter into the brain tissue, and bind to related pain receptors to achieve the purpose of analgesia. But all of these central nervous system analgesics may cause serious side effects, such as respiratory depression and addiction. Therefore, the use of local anesthetics without central nervous effect to control postoperative incision pain would be a major improvement. However, as mentioned above, the local anesthetic preparation for surgical incision analgesia must release the local anesthetic contained therein in a slow-release manner. According to this idea, Exparel, which was recently launched by Pacira Pharmaceuticals, Inc, uses a specially formulation containing local anesthetic bupivacaine to replace the central nervous analgesics or reduce the amount of the central nervous analgesics, which has been welcomed by doctors and patients. However, Exparel has many weaknesses: (1) the liposomes encapsulating bupivacaine in the preparation are unstable, so Exparel must be stored and transported under refrigeration; (2) Exparel must be injected complexly with up to 20 needles along the surgical incision, which is very inconvenient and time-consuming; (3) the postoperative analgesia is generally required for at least 2-3 days, but the effective analgesic effect of Exparel is only 24 hours. Therefore, it is also an urgent need to find a pharmaceutical preparation that can achieve long-term postoperative incision analgesia, can be conveniently used, and can be transported and stored at room temperature.

Content of the Present Invention

The technical problem to be solved in the present disclosure is to overcome the defect that the local anesthetic preparations in the prior art cannot achieve long-term continuous and safe analgesic effect, and to provide a new type of lipid pharmaceutical preparations and applications thereof.

The lipid pharmaceutical preparation of the present disclosure is mainly applied to the open human body surface requiring analgesia, and can take effect in a very short time, and can obtain continuous analgesic effect of 12, 24, 36, 48, 72 hours, or even longer. When the lipid pharmaceutical preparation of the present disclosure is applied to open human body surface pain, it can provide safe, long-term and effective analgesia.

In the present disclosure, the analgesic effect refers to the analgesic effect with statistical significance compared with a placebo without analgesic the active ingredient. The analgesic effect compared with the placebo can be measured with internationally accepted pain tests such as Visual Analog Scale, etc.

The lipid pharmaceutical preparation of the present disclosure also has the advantages of storage at room temperature and convenient use, etc. In analgesic applications, the lipid pharmaceutical preparation of the present disclosure can replace the traditional central nervous anesthetics, so as to avoid the serious side effects caused by central nervous anesthetics.

One of the technical solutions adopted by the present disclosure to address the above-mentioned needs is as follows:

The present disclosure provides a lipid pharmaceutical preparation, the lipid pharmaceutical preparation comprises a local anesthetic and a lipid substance, the mass percentage of the local anesthetic in the lipid pharmaceutical preparation is 2%-50%, and the local anesthetic is lidocaine, tetracaine, bupivacaine, articaine, cinchocaine, dibucaine, etidocaine, levobupivacaine, mepivacaine, prilocaine, ropivacaine, trimecaine, benzocaine, or procaine; the mass percentage of the lipid substance in the lipid pharmaceutical preparation is 30%-98%; the sum of the mass percentages of the components in the lipid pharmaceutical preparation is 100%.

In the above-mentioned lipid pharmaceutical preparation, the mass percentage of the local anesthetic in the lipid pharmaceutical preparation is preferably 3%-50%, 10%-50%, 20%-50%, 6%-50%, 6%-40%, 7%-35%, 8%-30%, 8%-24%, 10%-24% or 3%-8%, for example, it may be about 18%, about 25%, 18% or 25%.

In the above-mentioned lipid pharmaceutical preparation, the local anesthetic is preferably lidocaine, bupivacaine or tetracaine, and more preferably lidocaine.

In the above-mentioned lipid pharmaceutical preparation, the mass percentage of the lipid substance in the lipid pharmaceutical preparation is preferably 50%-98%, more preferably 55%-84%.

In the above-mentioned lipid pharmaceutical preparation, the melting temperature of the lipid pharmaceutical preparation is preferably above 37° C., more preferably above 45° C., even more preferably 45-200° C., further more preferably 45-80° C. The lipid pharmaceutical preparations within the melting temperature range mentioned above will not become free-flowing liquid after being applied into human tissue, thereby achieving better sustained-release effect.

In the above-mentioned lipid pharmaceutical preparation, the melting temperature of the lipid pharmaceutical preparation may also be 25-36° C., or 15-33° C. The lipid pharmaceutical preparation within the melting temperature range mentioned above can become viscous but fluid that can flow after being smeared to the surface of human tissue, so that it is easier to reach the surface of human tissue that requires analgesia. This is very important in certain analgesic applications. For example, wounds of the anus and/or colon adjacent to the anus after anorectal surgery are often very painful. After smearing the lipid pharmaceutical preparation with a melting temperature of 25-36° C. or 15-33° C. outside or inside the anus, the fluidity of the lipid pharmaceutical preparation enables it to contact all the surfaces or incisions inside and outside the anus that requires analgesia.

In the above-mentioned lipid pharmaceutical preparation, the lipid pharmaceutical preparation may also contain an anti-infection component; the anti-infection component is preferably one or more of chlorhexidine, antibiotics and sulfonamides, more preferably chlorhexidine. The mass percentage of chlorhexidine in the lipid pharmaceutical preparation is preferably 0.1%-5%, more preferably 0.2%-2%.

In the above-mentioned lipid pharmaceutical preparation, the lipid pharmaceutical preparation may also contain a water-soluble substance. The water-soluble substance may be glycerol, for example. The mass percentage of the water-soluble substance in the lipid pharmaceutical preparation is preferably 8%-12%.

In the above-mentioned lipid pharmaceutical preparation, the lipid pharmaceutical preparation may also contain chitin and/or derivative of chitin. The derivative of chitin is preferably carboxylated chitosan. The mass percentage of the carboxylated chitosan in the lipid pharmaceutical preparation is preferably 3%-5%. The above-mentioned lipid pharmaceutical preparation containing chitin and/or derivative of chitin have higher hardness and certain bacteriostatic ability.

In the above-mentioned lipid pharmaceutical preparation, the lipid pharmaceutical preparation may also contain hyaluronic acid or sodium hyaluronate. The mass percentage of the hyaluronic acid or sodium hyaluronate in the lipid pharmaceutical preparation is preferably 4%-8%. The hyaluronic acid may be uncrosslinked acid or crosslinked acid. The sodium hyaluronate may be uncrosslinked sodium hyaluronate or crosslinked sodium hyaluronate. The above-mentioned lipid pharmaceutical preparation containing hyaluronic acid or sodium hyaluronate can form a gel after contacting with and absorbing body fluids.

In the above-mentioned lipid pharmaceutical preparation, the lipid pharmaceutical preparation may also contain pH buffer pair. The mass percentage of the pH buffer pair in the lipid pharmaceutical preparation is preferably 4-18%, for example 12%. The pH buffer pair is preferably a pH buffer pair composed of disodium hydrogen phosphate and sodium dihydrogen phosphate, a pH buffer pair composed of dipotassium hydrogen phosphate and potassium dihydrogen phosphate, a pH buffer composed of sodium tetraborate and sodium hydroxide or a pH buffer pair composed of tris (hydroxymethyl)aminomethane and HCl, more preferably a pH buffer pair composed of disodium hydrogen phosphate and sodium dihydrogen phosphate or a pH buffer pair composed of sodium tetraborate and sodium hydroxide, and even more preferably a pH buffer pair composed of disodium hydrogen phosphate and sodium dihydrogen phosphate.

In the above-mentioned lipid pharmaceutical preparation, the lipid substance may be a lipid substance conventionally used in the art, and usually refers to one or more of animal fat, vegetable fat, and other fatty substances. The other fatty substances refer to medicinal or edible fatty substances other than animal fat and vegetable fat approved by the food and drug regulating agency of China, the United States, or other countries.

The animal fat is preferably lecithin and/or cholesterol. The vegetable fat is preferably soybean phospholipid, sunflower seed phospholipid or vegetable oil; the vegetable oil is preferably a vegetable oil with a melting point below 35° C., more preferably a vegetable oil with a melting point below 20° C. The vegetable oil is more preferably soybean oil.

In the above-mentioned lipid pharmaceutical preparation, preferably, the lipid substance is a combination of phospholipid and vegetable oil, more preferably a combination of lecithin and vegetable oil or a combination of lecithin and soybean oil. More preferably, the mass percentage of the phospholipid in the lipid pharmaceutical preparation is 40%-80%, and the mass percentage of the soybean oil in the lipid pharmaceutical preparation is 8%-50%.

In the present disclosure, the phospholipid refers to phospholipid extracted from any raw material, including lecithin, soybean phospholipid, sunflower seed phospholipid, and phospholipid from other sources.

In the above-mentioned lipid pharmaceutical preparation, preferably, the lipid pharmaceutical preparation comprises the following components (or consists of the following components) by mass percentage: 3%-50% of lidocaine, 30%-90% of phospholipid (for example, lecithin) and 3%-20% of vegetable oil. The vegetable oil is preferably a vegetable oil with a melting point below 35° C., more preferably a vegetable oil with a melting point below 20° C. The vegetable oil is more preferably soybean oil.

In the above-mentioned lipid pharmaceutical preparation, preferably, the lipid pharmaceutical preparation comprises the following components (or consists of the following components) by mass percentage: 5%-50% of lidocaine, 40%-85% of phospholipid (for example, lecithin) and 3%-20% of vegetable oil. The vegetable oil is preferably a vegetable oil with a melting point below 35° C., more preferably a vegetable oil with a melting point below 20° C. The vegetable oil is more preferably soybean oil.

In the above-mentioned lipid pharmaceutical preparation, preferably, the lipid pharmaceutical preparation comprises the following components (or consists of the following components) by mass percentage: 15%-25% of lidocaine, 65%-85% of phospholipid and 6%-15% of vegetable oil. The vegetable oil is preferably a vegetable oil with a melting point below 35° C., more preferably a vegetable oil with a melting point below 20° C. The vegetable oil is more preferably soybean oil.

In the above-mentioned lipid pharmaceutical preparation, preferably, the lipid pharmaceutical preparation comprises the following components (or consists of the following components) by mass percentage: 3%-8% of lidocaine, 40%-70% of phospholipid (for example, lecithin) and 25%-55% of vegetable oil. The vegetable oil is preferably a vegetable oil with a melting point below 35° C., more preferably a vegetable oil with a melting point below 20° C. The vegetable oil is more preferably soybean oil.

In the above-mentioned lipid pharmaceutical preparation, the lipid pharmaceutical preparation may also contain 8%-12% of glycerin by mass percentage.

In the above-mentioned lipid pharmaceutical preparation, the lipid pharmaceutical preparation may also contain 3%-5% (for example, 4%) of carboxylated chitosan by mass percentage.

In the above-mentioned lipid pharmaceutical preparation, the lipid pharmaceutical preparation may also contain 4%-8% of sodium hyaluronate by mass percentage.

In the above-mentioned lipid pharmaceutical preparation, preferably, the lipid pharmaceutical preparation comprises the following components (or consists of the following components) by mass percentage: 5%-30% (for example, 20%) of lidocaine, 55%-85% (for example, 72%) of phospholipid (for example, lecithin) and 8%-15% (for example, 8%) of sodium hyaluronate.

The second technical solution adopted by the present disclosure to address the above-mentioned needs is as follows:

The present disclosure also provides a lipid pharmaceutical preparation, the lipid pharmaceutical preparation comprises lidocaine and excipients, the mass percentage of the lidocaine in the lipid pharmaceutical preparation is 3%-50%, preferably 14%-50%, more preferably 15%-50%, the excipients are excipients that can be safely absorbed by the human body, and the excipients also contain a lipid substance, the mass percentage of the lipid substance in the lipid pharmaceutical preparation is above 30%, and is not 100%; the sum of the mass percentages of the components in the lipid pharmaceutical preparation is 100%;

after the lipid pharmaceutical preparation is embedded into human tissue, under the erosion of body fluids, the lidocaine in the lipid pharmaceutical preparation can be released in a slow-release manner from the lipid pharmaceutical preparation to the surface of the human tissue contacted by the lipid pharmaceutical preparation, and can make the patient's average blood drug concentration peak at the maximum dose not higher than 5000 ng/mL, preferably not higher than 2500 ng/mL, (for example, it may be not higher than 2000 ng/mL), the effective analgesic time is not shorter than 24 hours; wherein, the maximum dose is 0.5 g of the lipid pharmaceutical preparation/kg body weight.

In the process of research, the inventors of the present disclosure found that based on the needs of medicine and formulation stability, a formulation that meets the above ideal conditions can achieve long-term continuous and safe analgesic effect.

In the above-mentioned lipid pharmaceutical preparation, the excipients are preferably excipients in pharmaceutical preparations that have been approved for sale by the Food and Drug Administration of China, the United States, or other countries.

In the above-mentioned lipid pharmaceutical preparation, preferably, the effective analgesic time is not shorter than 48 hours.

In the above-mentioned lipid pharmaceutical preparation, preferably, the lipid substance is one or more of animal fat, vegetable fat, and other fatty substances. The other fatty substances refer to medicinal or edible fatty substances other than animal fat and vegetable fat approved by the Food and Drug Administration of China, the United States, or other countries.

Wherein, the animal fat is preferably lecithin and/or cholesterol.

Wherein, the vegetable fat is preferably soybean phospholipid, sunflower seed phospholipid or vegetable oil; the vegetable oil is preferably a vegetable oil with a melting point below 35° C., more preferably a vegetable oil with a melting point below 20° C. The vegetable oil is more preferably soybean oil.

Wherein, the lipid substance is preferably a combination of phospholipid and vegetable oil, more preferably a combination of lecithin and vegetable oil or a combination of lecithin and soybean oil.

In the above-mentioned lipid pharmaceutical preparation, preferably, the lipid pharmaceutical preparation does not have phase separation under the condition of high-temperature sterilization, and the temperature of the condition of high-temperature sterilization is above 121° C., for example, may be 121° C., and the time of the condition of high-temperature sterilization is above 15 minutes; for example, may be 15 minutes.

In the above-mentioned lipid pharmaceutical preparation, preferably, the lipid pharmaceutical preparation comprises the following components (or consists of the following components): lidocaine, phospholipid (for example, lecithin) and soybean oil, the mass percentage of the lidocaine in the lipid pharmaceutical preparation is 3%-25%, the mass percentage of the phospholipid (for example, lecithin) in the lipid pharmaceutical preparation is 50%-85% or 50%-77%, the mass percentage of the soybean oil in the lipid pharmaceutical preparation is 6%-50%, 6%-45%, 7%-25%, or 4%-25%. More preferably, the mass percentage of the lidocaine in the lipid pharmaceutical preparation is 15%-21%, 17%-21%, or 17%-20%, the phospholipid is lecithin, and the mass percentage of the phospholipid in the lipid pharmaceutical preparation is 65%-82% or 70%-75%, the mass percentage of the soybean oil in the lipid pharmaceutical preparation is 6%-12% or 8%-10%.

In the above-mentioned lipid pharmaceutical preparation, preferably, the lipid pharmaceutical preparation comprises the following components (or consists of the following components): lidocaine, phospholipid (for example, lecithin) and soybean oil, the mass percentage of the lidocaine in the lipid pharmaceutical preparation is 3%-12%, the mass percentage of the phospholipid (for example, lecithin) in the lipid pharmaceutical preparation is 40%-75%, the mass percentage of the soybean oil in the lipid pharmaceutical preparation is 20%-50%.

In the above-mentioned lipid pharmaceutical preparation, preferably, the lipid pharmaceutical preparation comprises the following components (or consists of the following components): lidocaine, phospholipid (for example, lecithin) and soybean oil, the mass percentage of the lidocaine in the lipid pharmaceutical preparation is 3%45%, the mass percentage of the phospholipid (for example, lecithin) in the lipid pharmaceutical preparation is 40%-80%, the mass percentage of the soybean oil in the lipid pharmaceutical preparation is 8%-50% or 8%-40%.

In the above-mentioned lipid pharmaceutical preparation, the lipid pharmaceutical preparation may also contain an anti-infection component. The anti-infection component is preferably one or more of chlorhexidine, antibiotics and sulfonamides, more preferably chlorhexidine. Wherein, the mass percentage of chlorhexidine in the lipid pharmaceutical preparation is preferably 0.1%-5%, more preferably 0.2%-2%. In this way, the risk of infection can be reduced.

After the lipid pharmaceutical preparation is embedded into human tissue, due to the concentration gradient of lidocaine and the erosion of human body fluids, lidocaine is released in a slow-release manner from the lipid pharmaceutical preparation to the surface of the human tissue contacted by the lipid pharmaceutical preparation; when at the maximum dose (0.5 g of the lipid pharmaceutical preparation/kg body weight), the average blood drug concentration peak is not higher than 5000 ng/mL, and more preferably not higher than 2500 ng/mL (the literature agrees that it is safe for the blood drug concentration peak to be less than 5000 ng/mL); the effective analgesic time is not shorter than 24 hours, even not shorter than 48 hours. Here, it should also be noted that the current mainstream postoperative analgesic method is to use an analgesic pump to deliver analgesics that act on the central nervous system into the body. The use time of the typical analgesic pump is 48 hours after the surgery. Therefore, the above-mentioned lipid pharmaceutical preparation that can provide effective analgesia time of 48 hours can replace an analgesic pump to a large extent.

The third technical solution adopted by the present disclosure to address the above-mentioned needs is as follows:

The present disclosure also provides a lipid pharmaceutical preparation, the lipid pharmaceutical preparation comprises lidocaine and excipients, the mass percentage of the lidocaine in the lipid pharmaceutical preparation is 3%-50%, the excipients are a lipid substance that can be safely absorbed by the human body or contain lipid substance that can be safely absorbed by the human body; the sum of the mass percentages of the components in the lipid pharmaceutical preparation is 100%.

In the above-mentioned lipid pharmaceutical preparation, preferably, the lipid substance is one or more of animal fat, vegetable fat, and other fatty substances.

Wherein, the animal fat is preferably lecithin and/or cholesterol.

Wherein, the vegetable fat is preferably soybean phospholipid, sunflower seed phospholipid or vegetable oil; the vegetable oil is preferably a vegetable oil with a melting point below 35° C., more preferably a vegetable oil with a melting point below 20° C. The vegetable oil is more preferably soybean oil.

Wherein, the lipid substance is preferably a combination of phospholipid and vegetable oil, the lipid substance is more preferably a combination of lecithin and vegetable oil or a combination of lecithin and soybean oil.

In the above-mentioned lipid pharmaceutical preparation, preferably, the lipid pharmaceutical preparation comprises the following components (or consists of the following components): lidocaine, phospholipid (for example, lecithin) and soybean oil, the mass percentage of the lidocaine in the lipid pharmaceutical preparation is 3%-25%, the mass percentage of the phospholipid (for example, lecithin) in the lipid pharmaceutical preparation is 50%-85% or 50%-77%, the mass percentage of the soybean oil in the lipid pharmaceutical preparation is 6%-50%, 6%-45%, 7%-25%, or 4%-25%. More preferably, the mass percentage of the lidocaine in the lipid pharmaceutical preparation is 15%-21% or 17%-20%, the phospholipid is lecithin, and the mass percentage of the phospholipid in the lipid pharmaceutical preparation is 65%-82% or 70%-75%, the mass percentage of the soybean oil in the lipid pharmaceutical preparation is 6%-12% or 8%-10%. The lipid pharmaceutical preparation is more suitable for embedding into the surgical incision.

In the above-mentioned lipid pharmaceutical preparation, preferably, the lipid pharmaceutical preparation comprises the following components (or consists of the following components): lidocaine, phospholipid (for example, lecithin) and soybean oil, the mass percentage of the lidocaine in the lipid pharmaceutical preparation is 3%-12%, the mass percentage of the phospholipid (for example, lecithin) in the lipid pharmaceutical preparation is 40%-75%, the mass percentage of the soybean oil in the lipid pharmaceutical preparation is 20%-50%.

In the above-mentioned lipid pharmaceutical preparation, preferably, the lipid pharmaceutical preparation comprises the following components (or consists of the following components): lidocaine, phospholipid (for example, lecithin) and soybean oil, the mass percentage of the lidocaine in the lipid pharmaceutical preparation is 3%-15%, the mass percentage of the phospholipid (for example, lecithin) in the lipid pharmaceutical preparation is 40%-80%, the mass percentage of the soybean oil in the lipid pharmaceutical preparation is 8%-50% or 8%-40%.

In the above-mentioned lipid pharmaceutical preparation, the lipid pharmaceutical preparation may also comprise an anti-infection component. The anti-infection component is preferably one or more of chlorhexidine, antibiotics and sulfonamides, more preferably chlorhexidine. Wherein, the mass percentage of chlorhexidine in the lipid pharmaceutical preparation is preferably 0.1%-5%, more preferably 0.2%-2%.

The fourth technical solution adopted by the present disclosure to address the above-mentioned needs is as follows:

The present disclosure also provides a lipid pharmaceutical preparation, the lipid pharmaceutical preparation comprises lidocaine, phospholipid (for example, lecithin), vegetable oil, and chlorhexidine; the mass percentage of the lidocaine in the lipid pharmaceutical preparation is 2%-25%, the mass percentage of the phospholipid (for example, lecithin) in the lipid pharmaceutical preparation is 40%-82% or 40%-80%, the mass percentage of the vegetable oil in the lipid pharmaceutical preparation is 15%-40%, the mass percentage of the chlorhexidine in the lipid pharmaceutical preparation is 0.1%-5%; the vegetable oil is preferably soybean oil; the mass percentage of the chlorhexidine in the lipid pharmaceutical preparation is preferably 0.2%-2%; the sum of the mass percentages of the components in the lipid pharmaceutical preparation is 100%.

Wherein, preferably, the mass percentage of the lidocaine in the lipid pharmaceutical preparation is 2%-21% or 2%-20%, the phospholipid is lecithin, and the mass percentage of the phospholipid in the lipid pharmaceutical preparation is 40%-82% or 50-70%, the mass percentage of the vegetable oil in the lipid pharmaceutical preparation is 6%-40%, 15%-50% or 15%-40%, the mass percentage of the chlorhexidine in the lipid pharmaceutical preparation is 0.2%-2%; the sum of the mass percentages of the components in the lipid pharmaceutical preparation is 100%. This lipid pharmaceutical preparation is more suitable to be applied to the painful areas of burns, the painful areas of burn scab removal, or the painful areas of incisions and wounds after anorectal surgery.

The fifth technical solution adopted by the present disclosure to address the above-mentioned needs is as follows:

The present disclosure also provides an application of a lipid pharmaceutical preparation in the preparation of medicines for treating open human body surface pain or open human tissue surface pain, the lipid pharmaceutical preparation is the above-mentioned lipid pharmaceutical preparation.

In the above-mentioned application, the open human body surface pain or open human tissue surface pain can be, for example, burn pain, pain during burn scab removal, incision and wound pain after anorectal surgery, or postoperative incision pain after non-anorectal surgery (such as thoracic and abdominal surgery, and orthopedic surgery).

In the above-mentioned application, after the lipid pharmaceutical preparation at a dose of less than or equal to 0.5 g of the lipid pharmaceutical preparation/kg body weight is applied to the open human body surface pain or open human tissue surface pain, the blood drug concentration peak can be less than 5000 ng/mL, the average blood drug concentration peak can even be not higher than 2500 ng/mL (for example, it may be not higher than 2000 ng/mL). Under the condition that the blood concentration of lidocaine does not exceed the above-mentioned peak value, the dose can exceed 0.5 g/kg body weight.

When the open human body surface pain or open human tissue surface pain is burn pain, pain during burn scab removal, or incision and wound pain after anorectal surgery, preferably, the application to the open human body surface pain or open human tissue surface pain refers to smearing the lipid pharmaceutical preparation to the open human body surface pain or open human tissue surface pain.

When the open human body surface pain or open human tissue surface pain is postoperative incision pain after non-anorectal surgery, preferably, the application to the open human body surface pain or open human tissue surface pain refers to embedding the lipid pharmaceutical preparation into the postoperative incision.

The sixth technical solution adopted by the present disclosure to address the above-mentioned needs is as follows:

The present disclosure also provides a treatment method using the lipid pharmaceutical preparation as described above, the treatment method is used to treat open human tissue surface pain.

In the above-mentioned treatment method, the open human tissue surface pain may be, for example, burn pain, pain during burn scab removal, incision and wound pain after anorectal surgery, or postoperative incision pain after non-anorectal surgery (such as thoracic and abdominal surgery, and orthopedic surgery)

In the above-mentioned treatment method, after the lipid pharmaceutical preparation at a dose of less than or equal to 0.5 g of the lipid pharmaceutical preparation/kg body weight is applied to the open human body surface pain or open human tissue surface pain, the blood drug concentration peak can be less than 5000 ng/mL, the average blood drug concentration peak can even be not higher than 2500 ng/mL (for example, it may be not higher than 2000 ng/mL). Under the condition that the blood concentration of lidocaine does not exceed the above-mentioned peak value, the dose can exceed 0.5 g/kg body weight.

When the open human tissue surface pain is burn pain, pain during burn scab removal, or incision and wound pain after anorectal surgery, preferably, the method applied to the open human tissue surface pain refers to smearing the lipid pharmaceutical preparation to the open human tissue surface pain.

When the open human tissue surface pain is postoperative incision pain after non-anorectal surgery, preferably, the method applied to the open human tissue surface pain refers to embedding the lipid pharmaceutical preparation into the postoperative incision.

The seventh technical solution adopted by the present disclosure to address the above-mentioned needs is as follows:

The present disclosure also provides an analgesic method using a lipid pharmaceutical preparation, the lipid pharmaceutical preparation is the above-mentioned lipid pharmaceutical preparation. The analgesic method comprises the following steps: applying and maintaining the lipid pharmaceutical preparation on the open human body surface;

or, maintaining the lipid pharmaceutical preparation on the surface of open human tissue surface.

In the above-mentioned analgesic method, the open human body surface pain or open human tissue surface pain may be, for example, burn pain, pain during burn scab removal, incision and wound pain after anorectal surgery, or postoperative incision pain after non-anorectal surgery.

In the above-mentioned analgesic method, when the pain to be treated is postoperative incision pain after non-anorectal surgery, the analgesic method preferably comprises the following step: applying the lipid pharmaceutical preparation to an unstitched or partially unstitched surgical incision. Or, when the pain to be treated is postoperative incision pain after non-anorectal surgery, the treatment method preferably comprises the following step: injecting or placing the lipid pharmaceutical preparation into the surgical incision or the tissue adjacent to the surgical incision. After the lipid pharmaceutical preparation is applied to the above-mentioned surgical incision or the tissue adjacent to the surgical incision, it will be slowly eroded by the contacted body fluid, thereby slowly releasing the local anesthetic contained therein. Since the erosion and release process is a slow process, the local anesthetic contained in the lipid pharmaceutical preparation will not cause excessive blood concentration, and can also provide a long-term analgesic effect.

In the above-mentioned analgesic method, when the pain to be treated is burn pain, pain during burn scab removal, or incision and wound pain after anorectal surgery, the analgesic method preferably comprises the following step: smearing and maintaining the lipid pharmaceutical preparation on the open human body surface or open human tissue surface. After contacting the open human body surface or the open human tissue surface, the lipid pharmaceutical preparation will be contacted by the open human body surface or the open human tissue surface, and the local anesthetic contained therein will diffuse into the open human body surface or the open human tissue surface due to the concentration gradient. Since the diffusion process is a slow process, the local anesthetic contained in the lipid pharmaceutical preparation will not cause excessive blood concentration, and can also provide a long-term analgesic effect.

In the present disclosure, the components in the lipid pharmaceutical preparation are uniformly mixed.

On the basis of not violating common knowledge in the field, the above-mentioned preferred conditions can be combined arbitrarily to obtain preferred examples of the present disclosure.

The positive progressive effects of the present disclosure are:

The lipid pharmaceutical preparation of the present disclosure is mainly applied to the open human body surface or open human tissue surface that requires analgesia, can take effect in a very short time, and can obtain continuous analgesic effect of 12, 24, 36, 48, 72 hours, or even longer. When the lipid pharmaceutical preparation of the present disclosure is applied to open human body surface or open human tissue surface pain, it can provide safe, long-term and effective analgesia.

The lipid pharmaceutical preparation of the present disclosure also has the advantages of storage at room temperature and convenient use, etc. In analgesic applications, the lipid pharmaceutical preparation of the present disclosure can replace the traditionally used central nervous anesthetics, so as to avoid the serious side effects caused by central nervous anesthetics.

DETAILED DESCRIPTION OF THE PREFERRED EMBODIMENT

The present disclosure will be further explained below by means of embodiments, but the present disclosure is not limited to the scope of the described embodiments. In the following embodiments, the experimental methods without specific conditions are selected according to conventional methods and conditions, or according to the commodity specifications.

Embodiment 1

A lipid pharmaceutical preparation. Its components are:

| Component | Mass percentage |
| --- | --- |
| Lecithin | 55% |
| Sodium dihydrogen phosphate | 0.07% |
| Disodium hydrogen phosphate | 11.93% |
| Lidocaine | 24% |
| Glycerin | 9% |

The preparation method of the lipid pharmaceutical preparation is as follows:

Sodium dihydrogen phosphate, disodium hydrogen phosphate, glycerin, lidocaine, and lecithin were put into a container. The same amount of water as the weight of lecithin was added. The mixture was stirred to get a paste. The paste was baked in an oven at 80° C. for 24 hours to evaporate the water contained in it, a cream-like lipid pharmaceutical preparation was obtained, which was recorded as lipid pharmaceutical preparation M.

Embodiment 2

A lipid pharmaceutical preparation. Its components are:

| Component | Mass percentage |
| --- | --- |
| Lecithin | 58% |
| Carboxylated chitosan | 4% |
| Lidocaine | 26% |
| Glycerin | 12% |

The preparation method of the lipid pharmaceutical preparation is as follows:

The carboxylated chitosan was first dissolved in 10 times its weight of water. Glycerin, lidocaine and lecithin were added. The mixture was stirred to get a paste. The paste was baked in an oven at 80° C. for 24 hours to evaporate the water contained in it, a solid lipid pharmaceutical preparation was obtained, which was recorded as lipid pharmaceutical preparation N.

Embodiment 3

A lipid pharmaceutical preparation. Its components are:

| Component | Mass percentage |
| --- | --- |
| Lecithin | 58% |
| Sodium hyaluronate | 4% |
| Lidocaine | 26% |
| Glycerin | 12% |

The preparation method of the lipid pharmaceutical preparation is as follows:

The sodium hyaluronate was first dissolved in 20 times its weight of water. Glycerin, lidocaine and lecithin were added. The mixture was stirred to get a paste. The paste was baked in an oven at 80° C. for 24 hours to evaporate the water contained in it, a solid lipid pharmaceutical preparation was obtained, which was recorded as lipid pharmaceutical preparation P.

Embodiment 4

A lipid pharmaceutical preparation. Its components are:

| Component | Mass percentage |
| --- | --- |
| Lecithin | 73% |
| Lidocaine | 18% |
| Soybean oil | 9% |

The preparation method of the lipid pharmaceutical preparation is as follows:

Lidocaine, soybean oil, and lecithin were put into a container. The mixture was heated to 125° C. and stirred, and then cooled to room temperature. A cream-like lipid pharmaceutical preparation was obtained, which was recorded as lipid pharmaceutical preparation Q. Lipid pharmaceutical preparation Q was soft solid at 45° C.

Embodiment 5

A lipid pharmaceutical preparation. Its components are:

| Component | Mass percentage |
|---|---|
| Lecithin | 59% |
| Lidocaine | 25% |
| Soybean oil | 8% |
| Glycerin | 8% |

The preparation method of the lipid pharmaceutical preparation is as follows:

Lidocaine, soybean oil, lecithin and glycerin were put into a container. The mixture was heated to 125° C. and stirred, and then cooled to room temperature. A cream-like lipid pharmaceutical preparation was obtained, which was recorded as lipid pharmaceutical preparation R.

Embodiment 6

A lipid pharmaceutical preparation. Its components are:

| Component | Mass percentage |
|---|---|
| Lecithin | 74% |
| Sodium dihydrogen phosphate | 0.07% |
| Disodium hydrogen phosphate | 11.93% |
| Lidocaine | 5% |
| Glycerin | 9% |

The preparation method of the lipid pharmaceutical preparation is as follows:

Sodium dihydrogen phosphate, disodium hydrogen phosphate, glycerin, lidocaine, and lecithin were put into a container. The same amount of water as the weight of lecithin was added. The mixture was stirred to get a paste. The paste was baked in an oven at 80° C. for 24 hours to evaporate the water contained in it, a cream-like lipid pharmaceutical preparation was obtained, which was recorded as lipid pharmaceutical preparation S.

Embodiment 7

A lipid pharmaceutical preparation. Its components are:

| Component | Mass percentage |
|---|---|
| Lecithin | 66% |
| Lidocaine | 17% |
| Soybean oil | 17% |

The preparation method of the lipid pharmaceutical preparation is as follows:

Lidocaine, soybean oil, and lecithin were put into a container. The mixture was heated to 125° C. and stirred, and then cooled to room temperature. A cream-like lipid pharmaceutical preparation was obtained, which was recorded as lipid pharmaceutical preparation T. The melting temperature of the lipid pharmaceutical preparation T is in the range of 25-36° C.

Embodiments 8-14

The lidocaine in Embodiments 1-7 is replaced with bupivacaine.

Embodiments 15-21

The lidocaine in Embodiments 1-7 is replaced with tetracaine.

Embodiment 22

A lipid pharmaceutical preparation. Its components are:

| Component | Mass percentage |
|---|---|
| Lecithin | 63.5% |
| Lidocaine | 15% |
| Soybean oil | 20% |
| Chlorhexidine (anti-infection component) | 1.5% |

The preparation method of the lipid pharmaceutical preparation is as follows:

Lidocaine, soybean oil, lecithin, and chlorhexidine were put into a container. The mixture was heated to 125° C. and stirred, and then cooled to room temperature. A cream-like lipid pharmaceutical preparation was obtained, which was recorded as lipid pharmaceutical preparation U. The melting temperature of the lipid pharmaceutical preparation U is in the range of 25-36° C., and it has bacteriostatic effect. Compared with the lipid pharmaceutical preparation Q, the lipid pharmaceutical preparation U has a lower melting temperature and a softer texture, so it is easier to be applied to open human body surfaces, such as large burned surfaces.

Embodiment 23

A lipid pharmaceutical preparation. Its components are:

| Component | Mass percentage |
|---|---|
| Lecithin | 56.5% |
| Lidocaine | 5% |
| Soybean oil | 38% |
| Chlorhexidine (anti-infection component) | 0.5% |

The preparation method of the lipid pharmaceutical preparation is as follows:

Lidocaine, soybean oil, lecithin, and chlorhexidine were put into a container. The mixture was heated to 125° C. and stirred, and then cooled to room temperature. A viscous oily lipid pharmaceutical preparation was obtained, which was recorded as lipid pharmaceutical preparation V. The melting temperature of the lipid pharmaceutical preparation V is in the range of 15-33° C., and it has analgesic and bacteriostatic effects simultaneously. Compared with the lipid pharmaceutical preparation Q, and even compared with the lipid pharmaceutical preparation U, the lipid pharmaceutical preparation V has a lower melting temperature and a softer texture, so it is easier to be applied to open human body surfaces, such as large burned surfaces.

Embodiments 24-30

A lipid pharmaceutical preparation. Its components are:

| Embodiment | Lidocaine | Lecithin | Soybean oil | Chlorhexidine | Carboxylated chitosan | Sodium hyaluronate | Total |
|---|---|---|---|---|---|---|---|
| 24 | 2 wt % | 90 wt % | 7.9 wt % | 0.1 wt % | / | / | 100 wt % |
| 25 | 3 wt % | 85 wt % | 9 wt % | 0.2 wt % | / | 2.8 wt % | 100 wt % |
| 26 | 5 wt % | 80 wt % | 13 wt % | 2 wt % | / | / | 100 wt % |
| 27 | 7 wt % | 75 wt % | 10 wt % | / | 4 wt % | 4 wt % | 100 wt % |
| 28 | 15 wt % | 54 wt % | 30 wt % | 1 wt % | / | / | 100 wt % |
| 29 | 25 wt % | 55 wt % | 19 wt % | 1 wt % | / | / | 100 wt % |
| 30 | 30 wt % | 50 wt % | 20 wt % | / | / | / | 100 wt % |

The preparation method of the lipid pharmaceutical preparation is as follows:

Each component is put into a container. The mixture is heated to 125° C. and stirred, and then cooled to room temperature. A viscous oily lipid pharmaceutical preparation is obtained.

The lipid pharmaceutical preparations of Embodiments 1-30 all have the following properties: in the above-mentioned lipid pharmaceutical preparations, the excipients (components other than a local anesthetic and/or chlorhexidine) are excipients that can be safely absorbed by the human body; after the above-mentioned lipid pharmaceutical preparations are embedded into human tissue or applied on open human body surface, under the erosion of body fluids, the lidocaine therein can be released from the above-mentioned lipid pharmaceutical preparation in a slow-release manner to the surface of the human tissue contacted by the above-mentioned lipid pharmaceutical preparation, and can make the patient's average blood drug concentration peak at the maximum dose not higher than 5000 ng/mL, more preferably not higher than 2500 ng/mL; the effective analgesia time is not less than 24 hours; wherein, the maximum dose is 0.5 g of the above-mentioned lipid pharmaceutical preparation/kg body weight.

Effect Embodiment 1

At the end of a patient's abdominal surgery, the fascia and muscle layer were first sutured by surgeons, and then the lipid pharmaceutical preparation M stored in a syringe was extruded and was put into the surgical incision (the length of incision was 10 cm, the extruded lipid pharmaceutical preparation M strip was also 10 cm long, so a 10 cm lipid pharmaceutical preparation M weighing 4 g was placed along the length of the incision), then the cortex was sutured.

The lidocaine in the lipid pharmaceutical preparation M, which was placed in the surgical incision, was slowly released into the incision tissue, thereby anesthetizing the incision tissue for a long time. The patient basically felt no pain for 72 hours after the surgery. Patients who had the same surgery would have severe pain for at least three days after surgery without any analgesics. The experience of this patient showed that using the lipid pharmaceutical preparation M according to the above-mentioned method of application can provide effective analgesia for at least 72 hours.

Effect Embodiment 2

At the end of a patient's abdominal surgery, the fascia and muscle layer were first sutured by surgeons, and then the lipid pharmaceutical preparation Q stored in a syringe was extruded and was put into the surgical incision (the length of incision was 10 cm, and 3 g of lipid pharmaceutical preparation Q was placed evenly along the length of the incision), then the cortex was sutured.

The lidocaine in the lipid pharmaceutical preparation Q, which was placed in the surgical incision, was slowly released into the incision tissue. The patient basically felt no pain for 72 hours after the surgery. Patients who had the same surgery would have severe pain for at least three days after surgery without any analgesics. The experience of this patient showed that using the lipid pharmaceutical preparation Q according to the above-mentioned method of application can provide effective analgesia for at least 72 hours.

Effect Embodiment 3

At the end of a patient's abdominal surgery, the fascia and muscle layer were first sutured by surgeons, and then the lipid pharmaceutical preparation S stored in a syringe was extruded and was put into the surgical incision (the length of incision was 12 cm, and 8 g of lipid pharmaceutical preparation S was placed evenly along the length of the incision), then the cortex was sutured.

The lidocaine in the lipid pharmaceutical preparation S, which was placed in the surgical incision, was slowly released into the incision tissue. The patient basically felt no pain for 72 hours after the surgery. Patients who had the same surgery would have severe pain for at least three days after surgery without any analgesics. The experience of this patient showed that the lipid pharmaceutical preparation S can provide effective analgesia for at least 72 hours.

Effect Embodiment 4

A patient's second-degree burn wound surface was very painful and was at risk of infection. The lipid pharmaceutical preparation U was smeared on the wound surface by the doctor, and then the preparation layer was covered with gauze.

Lidocaine and chlorhexidine (anti-infection component) in the lipid pharmaceutical preparation U smeared on the wound surface were slowly released into the wound surface tissue, thereby achieving the purpose of long-term analgesia. The patient basically felt no pain for 24 hours after surgery, and the risk of infection was greatly reduced.

Effect Embodiment 5

A patient's wound surface after anal fistula surgery was very painful and was at risk of infection. The lipid pharmaceutical preparation U was smeared on the wound surface by the doctor. The patient's pain, especially the pain during defecation, was greatly reduced.

Lidocaine and chlorhexidine (anti-infection component) in the lipid pharmaceutical preparation U smeared on the wound surface were slowly released into the wound surface tissue, thereby achieving the purpose of long-term analgesia and prevention of infection.

Effect Embodiment 6

A patient's second-degree burn wound surface was very painful and was at risk of infection. The lipid pharmaceutical preparation V was smeared on the wound surface by the doctor, and then the preparation layer was covered with gauze.

Lidocaine and chlorhexidine (anti-infection component) in the lipid pharmaceutical preparation V smeared on the wound surface were slowly released into the wound surface tissue, thereby achieving the purpose of long-term analgesia. The patient basically felt no pain for 24 hours after surgery, and the risk of infection was greatly reduced.

The lipid pharmaceutical preparation V has a lower viscosity than the lipid pharmaceutical preparation U, so it is easier to be smeared on the burn wound.

Effect Embodiment 7

The lipid pharmaceutical preparations N, P, Q and R, the lipid pharmaceutical preparations of Embodiments 8-21 and Embodiments 24-30, are used for surgical incisions of patients, can also provide effective analgesia for at least 72 hours.

Effect Embodiment 8

3 g of the lipid pharmaceutical preparation Q of the present disclosure was placed into a 5 cm surgical incision (t=0 at this time) in the abdomen of a pig weighing about 10 kg that had not been sutured, and then cortical suture was performed. In this way, the lipid pharmaceutical preparation Q was sealed between the sutured fascia layer and the cortex. Wherein, the lipid pharmaceutical preparation Q contained 18 wt % of lidocaine (3 g contained 540 mg lidocaine in total), so the dose of lidocaine obtained by the pig was 54 mg/kg.

At pre-set time points over the next 72 hours, the venous blood of the pig was collected and the concentration of lidocaine in the blood sample was measured by the LC-MS method.

The above experiment with two other pigs was repeated.

The average blood drug concentrations (ng/mL) of the three pigs at these time points are listed in the table below.

In the table below, the rightmost column lists blood concentrations over time after a 60 mg/kg dose of lidocaine was administered by the method of intramuscular infusion at a constant rate for 2 hours reported by Ikeda et al. in the reference (Pharmacokinetics of Lidocaine, Bupivacaine, and Levobupivacaine in Plasma and Brain in Awake Rats; Yuko Ikeda et al.; Anesthesiology 2010; 112:1396-1403). In addition, since Ikeda et al. only reported the data of the first 4 hours, the data after 4 hours was calculated according to the industry-recognized theoretical calculation of lidocaine elimination half-life=2 hours, wherein, the English for elimination half-life is elimination half-life.

| Time/hour | After the lipid pharmaceutical preparation Q of the present disclosure was put into the incision tissue at t = 0, the blood drug concentration of lidocaine/(ng/mL) Dose 54 mg/kg Average of the three pigs | After the preparation in the reference was infused into the muscle at a constant rate for t = 0-2 hours, the blood drug concentration of lidocaine/(ng/mL) Dose 60 mg/kg |
|---|---|---|
| 0 | 0 | 0 |
| 0.25 | 84 | 1900 |
| 0.5 | 133 | 5800 |
| 1 | 322 | 8200 |
| 2 | 494 | 10500 |
| 4 | 531 | 800 |
| 6 | 524 | 400 |
| 8 | 443 | 200 |
| 12 | 331 | 100 |
| 15 | 287 | 35.3 |
| 18 | 257 | 6.25 |
| 24 | 178 | 1.6 |
| 30 | 140 | 0.2 |
| 36 | 86 | 0 |
| 42 | 56 | 0 |
| 48 | 37 | 0 |
| 54 | 27 | 0 |
| 60 | 19 | 0 |
| 66 | 15 | 0 |
| 72 | 14 | 0 |

It can be seen from the data in the above table that although the doses are similar, the blood drug concentration peak of lidocaine caused by the lipid drug preparation Q is much lower than the blood drug concentration peak of lidocaine caused by the preparation used in the reference literature (industry recognized when the blood drug concentration of lidocaine greater than or equal to 5000 ng/mL would cause side effects such as increased heart rate), and the duration of the former is much longer than the latter.

Although the specific embodiments of the present disclosure are described above, those skilled in the art should understand that these are only illustrative examples, the scope of protection of the present disclosure is limited by the attached claims. Those skilled in the art can make various changes or modifications to these embodiments without deviating from the principle and essence of the present disclosure, but these changes and modifications all fall within the scope of protection of the present disclosure.

The singular or plural nouns do not limit the scope of this application.

What is claimed is:
1. A lipid pharmaceutical preparation, wherein, the lipid pharmaceutical preparation comprises a local anesthetic, a lipid substance and sodium hyaluronate; and the local anesthetic is lidocaine;
  the lipid substance is lecithin;
  wherein the lipid pharmaceutical preparation comprises by mass percentage: 5%-30% of lidocaine, 55%-85% of lecithin and 8%-15% of sodium hyaluronate.
2. The lipid pharmaceutical preparation according to claim 1, wherein, the mass percentage of the local anesthetic in the lipid pharmaceutical preparation is 8%-30%, 8%-24%, or 10%-24%.
3. The lipid pharmaceutical preparation according to claim 1, wherein, the melting temperature of the lipid pharmaceutical preparation is above 37° C.;
  or, the melting temperature of the lipid pharmaceutical preparation is 25-36° C.;
  or, the melting temperature of the lipid pharmaceutical preparation is 15-33° C.

4. The lipid pharmaceutical preparation according to claim 3, wherein, the melting temperature of the lipid pharmaceutical preparation is above 45° C.

5. The lipid pharmaceutical preparation according to claim 1, wherein, the lipid pharmaceutical preparation further contains an anti-infection component.

6. The lipid pharmaceutical preparation according to claim 5, wherein, the anti-infection component is one or more of chlorhexidine, antibiotics or sulfonamides;
or, the anti-infection component is chlorhexidine, and the mass percentage of chlorhexidine in the lipid pharmaceutical preparation is 0.1%-5%.

7. The lipid pharmaceutical preparation according to claim 1, wherein, the lipid pharmaceutical preparation further contains a water-soluble substance;
or, the lipid pharmaceutical preparation further contains one or more selected from the group consisting of chitin and a derivative of chitin, the derivative of chitin is carboxylated chitosan;
or, the lipid pharmaceutical preparation further contains a pH buffer pair.

8. A method for treating open human body surface pain or open human tissue surface pain in a subject in need thereof, comprising: administering a lipid pharmaceutical preparation to the subject, wherein, the lipid pharmaceutical preparation is the lipid pharmaceutical preparation according to claim 1.

9. The method according to claim 8, wherein, the open human body surface pain or open human tissue surface pain is burn pain, pain during burn scab removal, incision and wound pain after anorectal surgery, or postoperative incision pain after non-anorectal surgery;
or, after the lipid pharmaceutical preparation at a dose of less than or equal to 0.5 g of the lipid pharmaceutical preparation/kg body weight is applied to the open human body surface pain or open human tissue surface pain, the blood drug concentration peak is less than 5000 ng/mL, or is not higher than 2500 ng/mL.

10. An analgesic method using a lipid pharmaceutical preparation, the lipid pharmaceutical preparation is the lipid pharmaceutical preparation according to claim 1; the analgesic method comprises the following steps:
applying the lipid pharmaceutical preparation on an open human body surface pain; or, applying the lipid pharmaceutical preparation on an open human tissue surface pain.

11. The analgesic method according to claim 10, wherein the open human body surface pain or open human tissue surface pain is burn pain, pain during burn scab removal, incision and wound pain after anorectal surgery, or postoperative incision pain after non-anorectal surgery;
or, when the pain to be treated is postoperative incision pain after non-anorectal surgery, the analgesic method comprises the following step: applying the lipid pharmaceutical preparation to an unstitched or partially unstitched surgical incision; or, when the pain to be treated is postoperative incision pain after non-anorectal surgery, the analgesic method comprises the following step: injecting or placing the lipid pharmaceutical preparation into the surgical incision or a tissue adjacent to the surgical incision;
or, when the pain to be treated is burn pain, pain during burn scab removal, or incision and wound pain after anorectal surgery, the analgesic method comprises the following step: smearing the lipid pharmaceutical preparation on the open human body surface pain or open human tissue surface pain.

12. The lipid pharmaceutical preparation according to claim 1, wherein,
the effective analgesic time is not shorter than 24 hours.

13. A lipid pharmaceutical preparation, wherein, the lipid pharmaceutical preparation comprises the following components: lidocaine, lecithin and soybean oil,
wherein, the mass percentage of the lidocaine in the lipid pharmaceutical preparation is 15%-21%, 17%-21%, or 17%-20%, the mass percentage of the lecithin in the lipid pharmaceutical preparation is 62%-77% or 70%-75%, and the mass percentage of the soybean oil in the lipid pharmaceutical preparation is 6%-12% or 8%-10%; and wherein
after the lipid pharmaceutical preparation is embedded into human tissue of a subject, under the erosion of body fluids, the lidocaine in the lipid pharmaceutical preparation is released in a slow-release manner from the lipid pharmaceutical preparation to the surface of the human tissue contacted by the lipid pharmaceutical preparation, and makes the subject's average blood drug concentration peak at the maximum dose not higher than 5000 ng/mL, the effective analgesic time is not shorter than 24 hours; and wherein, the maximum dose is 0.5 g of the lipid pharmaceutical preparation/kg body weight.

14. The lipid pharmaceutical preparation according to claim 13, wherein, the lipid pharmaceutical preparation further contains an anti-infection component.

15. The lipid pharmaceutical preparation according to claim 14, wherein, the anti-infection component is one or more of chlorhexidine, antibiotics or sulfonamides;
or, the anti-infection component is chlorhexidine, and the mass percentage of chlorhexidine in the lipid pharmaceutical preparation is 0.1%-5%.

16. A treatment method comprising administering the lipid pharmaceutical preparation according to claim 13 to a subject in need thereof, wherein the treatment method is used to treat open human tissue surface pain in the subject.

17. The treatment method according to claim 16, wherein, the open human tissue surface pain is burn pain, pain during burn scab removal, incision and wound pain after anorectal surgery, or postoperative incision pain after non-anorectal surgery;
or, after the lipid pharmaceutical preparation at a dose of less than or equal to 0.5 g of the lipid pharmaceutical preparation/kg body weight is applied to the open human tissue surface pain, the blood drug concentration peak is less than 5000 ng/mL, or not higher than 2500 ng/mL;
or, when the open human tissue surface pain is burn pain, pain during burn scab removal, or incision and wound pain after anorectal surgery, the administering step comprises smearing the lipid pharmaceutical preparation to the open human tissue surface pain; or, when the open human tissue surface pain is postoperative incision pain after non-anorectal surgery, the administering step comprises embedding the lipid pharmaceutical preparation into the postoperative incision.

18. An analgesic method using a lipid pharmaceutical preparation, the lipid pharmaceutical preparation is the lipid pharmaceutical preparation according to claim 13; the analgesic method comprises the following steps:
applying the lipid pharmaceutical preparation on an open human body surface pain; or, applying the lipid pharmaceutical preparation on an open human tissue surface pain.

19. The analgesic method according to claim 18, wherein, the open human body surface pain or open human tissue surface pain is burn pain, pain during burn scab removal, incision and wound pain after anorectal surgery, or postoperative incision pain after non-anorectal surgery;
- or, when the pain to be treated is postoperative incision pain after non-anorectal surgery, the analgesic method comprises the following step: applying the lipid pharmaceutical preparation to an unstitched or partially unstitched surgical incision; or, when the pain to be treated is postoperative incision pain after non-anorectal surgery, the analgesic method comprises the following step: injecting or placing the lipid pharmaceutical preparation into the surgical incision or a tissue adjacent to the surgical incision;
- or, when the pain to be treated is burn pain, pain during burn scab removal, or incision and wound pain after anorectal surgery, the analgesic method comprises the following step: smearing the lipid pharmaceutical preparation on the open human body surface pain or open human tissue surface pain.

* * * * *